United States Patent [19]

Cornu et al.

[11] Patent Number: 4,604,393

[45] Date of Patent: Aug. 5, 1986

[54] PHENYLOXOALKYL PIPERIDINES AND THE PHARMACEUTICAL COMPOSITIONS CONTAINING THEM

[76] Inventors: Pierre-Jean Cornu, 100, Avenue Kleber, F-75116, Paris; Claude Perrin, 5, rue de 1-Avenir, F-91400, Orsay; Bernard Dumaitre, 24, rue Chemin Vert., F-93000, Bobigny; Gilles Streichenberger, 30, boulevard du Chateau, F-92200, Neuilly sur Seine, all of France

[21] Appl. No.: 575,022

[22] Filed: Jan. 30, 1984

[51] Int. Cl.$^4$ .................. C07D 211/26; C07D 211/58; C07D 405/06; C07D 413/12; C07D 413/14; A61K 31/535; A61K 31/445

[52] U.S. Cl. .................................... 514/229; 544/129; 544/130; 546/197; 546/207; 546/223; 546/230; 514/232; 514/237; 514/326; 514/331; 514/329

[58] Field of Search .............. 546/230, 223, 197, 207; 424/267; 544/130, 129; 514/237, 329, 229, 232, 326, 331

Primary Examiner—Norma S. Milestone
Attorney, Agent, or Firm—Omri M. Behr

[57] ABSTRACT

This invention relates to novel piperidines substituted on the nitrogen atom with a (phenyloxo alkyl) group as well as the processes for their production.

6 Claims, No Drawings

PHENYLOXOALKYL PIPERIDINES AND THE PHARMACEUTICAL COMPOSITIONS CONTAINING THEM

SUMMARY

The present invention provides the compounds of formula I

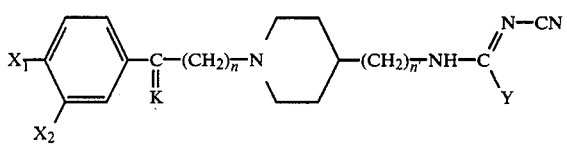

wherein $X_1$ and $X_2$ are substituents
K is the residue of a free or blocked carbonyl function
Y is selected from the group consisting of a radical $ZR_5$ (wherein Z is oxygen or sulphur and $R_5$ is a lower alkyl radical) and an amino group
n and n' are integers ranging from 0 to 3

The compounds of formula I and the salts thereof are useful as active ingredients of drugs.

DETAILED EMBODIMENTS OF THE INVENTION

This invention relates to novel piperidines substituted on the nitrogen atom with a phenyloxoalkyl group, the piperidine ring of which further bears an alkylguanidine or alkylisourea group.

Specifically this invention relates to phenyloxoalkyl piperidines of formula I

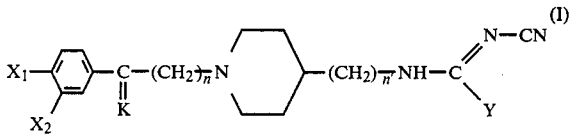

wherein $X_1$ and $X_2$ the same or different, are hydrogen, a lower alkyl radical, a lower alkoxy radical, a halogen, or a trifluoromethyl radical or $X_1$ and $X_2$ together are an alkylene dioxy group.
K is the oxygen of a carbonyl function or a group

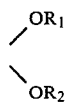

(wherein $R_1$ and $R_2$ are lower alkyl radicals or form together a lower alkylene chain).
Y is a radical selected from the group consisting of a radical $ZR_5$ (wherein Z is oxygen or sulphur and $R_5$ is a lower alkyl radical) and a radical

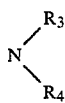

(wherein $R_3$ is a lower alkyl, a lower alkenyl, a lower cycloalkyl, or a heterocyclanyl radical having 5, 6 or 7 links $R_4$ is hydrogen, a lower alkyl radical or the acyl residue of an organic carboxylic acid,
or $R_3$ and $R_4$ together are the alkylene chain of a nitrogenous heteroring which may include another hetero atom)
n is equal to 1, 2 or 3
and n' is equal to 0 or 1.

Moreover when Y is an aminogroup of the formula

the formula I merely shows one of the optional structures of the cyanoguanidines. In acidic medium any of the nitrogen atoms of the guanidine group may be protonated. Therefore the compounds according to this invention may exist under the two tautomeric forms iminocyanoamine and (aminocyano)imine.

The cyano group may further be located on one or on the other side of the plane determined by the double bond —C=N—. It may exist as an isomer of the syn or anti type.

The tautomeric forms and the isomeric forms are part of this invention.

This invention also provides the acid addition salts of the compounds of formula I with a mineral or organic acid, preferably a therapeutically-compatible acid.

This invention also provides the optically-active isomers of the compounds of formula I as well as the diastereoisomers of the compounds of formula I.

Among the acid addition salts of the compounds of formula I may more particularly cite the hydrochlorides, the hydrobromides, the sulphates, nitrates, phosphates, thiosulphates, formates, acetates, maleates, fumarates, benzoates, dichloro 2,6-benzoates, citrates, tartarates, (methoxy salicylates), 3,4,5-trimethoxy benzoates, vanillates, the O-carbethoxy syringates, the naphthoates, the benzene sulphonates, the methane sulphonates, the isothionates, the nicotinates, the isonicotinates and the glucose-phosphates.

When $R_3$ and $R_4$ together are the alkylene chain of a nitrogenous heteroring, they form with the nitrogen atom to which they are bound, a pyrrolidinyl radical, a piperidinyl, a hexamethylene imino, a heptamethylene imino or when they include an extra heteroatom, a morpholino radical, a tetrahydrothiazinyl, a hexahydropyrimidinyl, a hexahydropyrazinyl, a pyrazolidinyl or an imidazolidinyl radical.

As far as the invention is concerned, a lower alkyl radical is a hydrocarbon radical having from 1 to 6 carbon atoms in a straight or branched chain, as for example methyl, ethyl, isopropyl, sec butyl, tert butyl, pentyl, neo pentyl, and n-hexyl.

A lower alkoxy radical has from 1 to 6 carbon atom in the alkyl moiety which may be straight or branched as for example a methoxy, ethoxy, isopropoxy, tert butoxy or pentyloxy.

An acyl radical derives from an organic carboxylic acid having from 1 to 12 carbon atoms as for example an alkyl carboxylic acid, an aryl alkylcarboxylic acid, a cycloalkyl carboxylic acid, an arylcarboxylic acid, and a hetero aryl carboxylic acid. In this respect may be specifically cited an acetyl residue, a butyryl residue, a benzoyl residue, a 3,4,5-trimethoxy benzoyl residue, a cyclopropylcarbonyl residue or a nicotinoyl residue.

The meanings given to the parameters n and n' play an important role in the pharmacological properties of the compounds of formula I. The intensity or the duration of action of the compounds according to this invention may be modulated by modifying the length of the alkyl chain in one or the other part of the molecule.

Among the compounds of formula I, the following 4 sub-groups may be more precisely differentiated which are presently the preferred ones (1) The N-cyano N'-(alkyl guanidinyl)piperidines of formula $I_A$

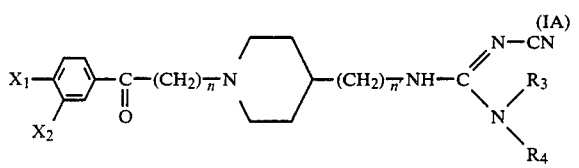

wherein the substituents $X_1$, $X_2$, $R_3$, $R_4$, n and n' have the above-given definitions.

(2) The N-cyano isoureas and isothioureas of the formula $I_B$

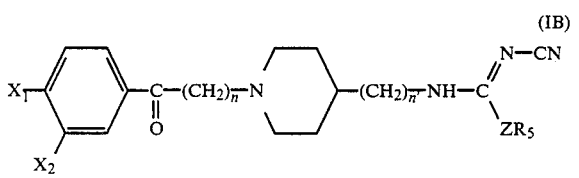

wherein $X_1$, $X_2$, $R_5$, n and n' have the above-given definitions.
and Z is an oxygen or a sulphur atom.

(3) The ketals of N-cyano $ZR_5$-isoureyl piperidines of the formula $I_C$

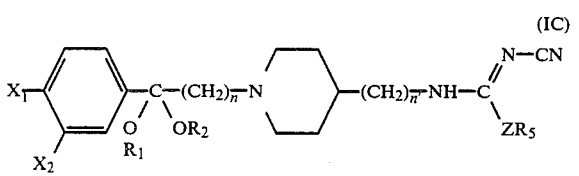

wherein $R_1$ and $R_2$ are a lower alkyl radical or together form a lower alkylene chain
and the substituents $X_1$, $X_2$, Z, $R_5$, n and n' have the above-given meanings.

(4) The ketals of cyanoguanidinyl piperidines of the formula $I_D$

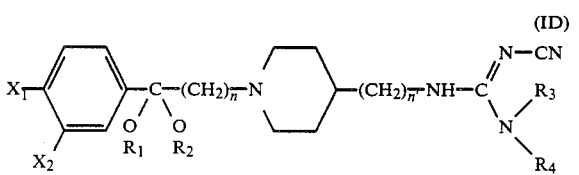

wherein the substituents $X_1$, $X_2$, $R_1$, $R_2$, $R_3$, $R_4$, n and n' have the above-given definition.

Among the compounds according to this invention it may be specifically cited:
1-[4-p.fluorophenyl 4-oxobutyl-1)]4-[(N-cyano N'-methyl guanidinyl)methyl]piperidine
1-[4-p.fluorophenyl 4-oxobutyl-1)]4-[(N-cyano N'-allyl guanidinyl)methyl]piperidine
1-[4-p.fluorophenyl 4-oxobutyl-1)]4-[(N-cyano N'cyclopropyl guanidinyl)methyl]piperidine
1-[(4-p.fluorophenyl 4-ethylenedioxy)butyl-1]4-[(N-cyano N-allyl guanidinyl)methyl]piperidine
1-[(4-p.fluorophenyl 4-ethylenedioxy)butyl-1]4-[(N-cyano S-methylisothioureido)methyl]piperidine The compounds according to this invention are endowed with interesting pharmacological properties, namely with antihypertensive and vasodilating actions connected with a sedative action on the Central Nervous System. Due to their high level of efficiency, the compounds of formula I or the acid addition salts thereof have use in human or animal therapy as active ingredients of medicines intended to counteract or to decrease the noxious effects of the hypertensive condition or to improve conditions in peripheric or cerebral vascular diseases.

For these purposes they are utilized in the form of pharmaceutical compositions designed for the administration by parenteral, oral, rectal or sublingual ways.

These pharmaceutical compositions include as active ingredient at least one compound of formula I or an acid addition salt thereof, in adjunction or admixture with an inert pharmaceutically-acceptable carrier or vehicle.

As preferred means of administration there may be cited uncoated or coated tablets, capsules, soft gelatine capsules, multi-cores tablets, drops, drinkable suspensions or solutions, injectable suspensions or solutions packed in ampules, multidoses, flasks or in autoinjectable syringes, suppositories, sublingual tablets.

The pharmaceutical compositions according to this invention may also include one or several active ingredients having a similar, a complementary or synergistic action. In this regard there may be added a diuretic agent of thiazidic structure or of triaminopteridine structure or a beta-blocking agent such as propranolol, pindolol or atenolol.

The daily dose may vary within a broad range with respect to the therapeutic use, the way of administration, the weight of the patient and the duration of the hypertensive condition. Usually in the adult the dosology ranges from 0.1 to 50 mg per unit dosage and from 0.1 to 150 mg per day.

In a preferred manner the pharmaceutical compositions, according to this invention include from 0.1 mg to 20 mg of active ingredient per unit dosage.

This invention also extends to a process for producing the compounds of formula I characterized in that an 4-aminopiperidine of formula II

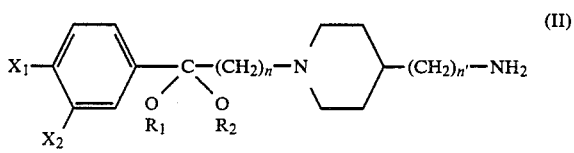

wherein the substituents $X_1$, $X_2$, n and n' have the previously-given definitions
$R_1$ and $R_2$ are a lower alkyl radical or together are a lower alkylene chain,
are reacted with a cyanoiminating reagent selected from the group consisting of
alkyl cyanoimino isodithiocarbonates of the formula III

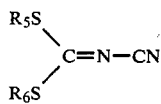

wherein $R_5$ and $R_6$ are a lower alkyl radical
and alkyl mixed cyanoimino isothiocarbonates of the formula IV

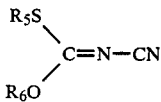

wherein $R_5$ and $R_6$ have the previously given definitions
to produce an isothiourea or an isourea of the formula $I_C$

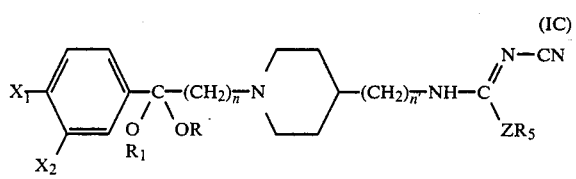

wherein the substituents $X_1$, $X_2$, $R_1$, $R_5$, n and n' have the above given meanings
and Z is an oxygen or a sulphur atom which may—when desired—be condensed with a primary or secondary amine of the formula

to obtain the cyanoguanidine of formula $I_D$

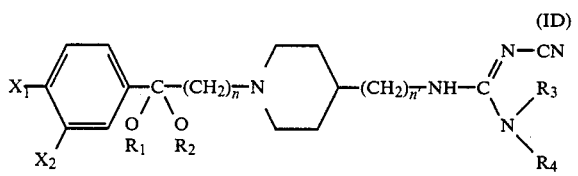

wherein the substituents $X_1$, $X_2$, $R_1$, $R_2$, $R_3$, $R_5$, n and n' are defined as previously
and $R_4$ is a hydrogen or a lower alkyl radical
or $R_3$ and $R_4$ together are the alkylene chain of a nitrogenous heteroring
which may further be hydrolysed in acidic medium to produce the free carbonyl derivative of formula $I_A$

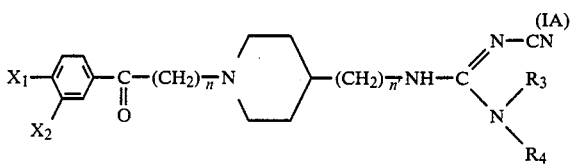

in which $X_1$, $X_2$, $R_3$, $R_4$, n and n' have the previously given definitions
which may, when $R_4$ is a hydrogen, be acylated by means of a functional derivative of a carboxylic acid to produce a N'-acyl N-cyanoguanidine of the formula $I_A$

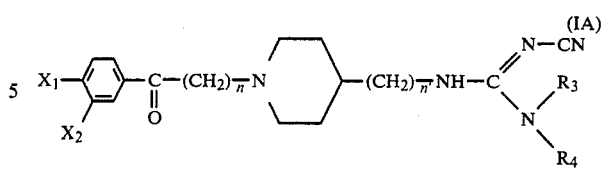

wherein $R_3$, n and n' have the above-given definitions
and $R_4$ is the acyl residue of a carboxylic acid having from 1 to 12 carbon atoms
or be resolved by means of an optically-active organic acid into its optically-active isomers
or be salified by adding a mineral or organic acid.

The starting 4-amino piperidines of formula II may be obtained when n' is zero according to a process which comprises condensing a reactive ester of a phenyl oxo alkyl of formula V

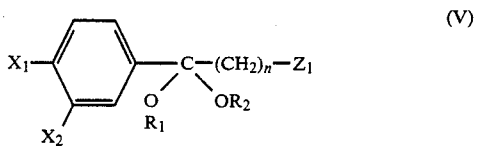

wherein $X_1$, $X_2$, $R_1$, $R_2$ and n have the previously-given definitions
and $Z_1$ is an easily-split ester
with a blocked piperidine of the formula VI

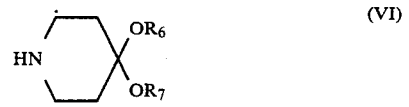

wherein $R_6$ and $R_7$, the same or different, are a lower alkyl radical or together form an alkylene chain of 2 to 4 carbon atoms
to produce a blocked phenyl(oxo alkyl)piperidine,
the ketonic function of which is selectively freed by functional exchange with an α-ketoacid to obtain a piperidine of formula VII

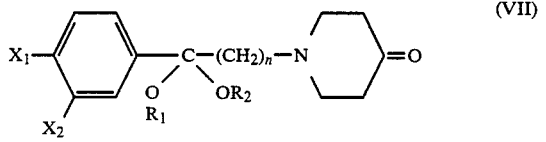

wherein the substituents $X_1$, $X_2$, $R_1$, $R_2$ and n have the same definitions as above,
condensing the latter with hydroxylamine or a salt thereof to produce the corresponding oxime which is further reduced by means of a mixed hydride to the corresponding amino derivative.

The starting 4-aminopiperidines of formula II may also be produced—when n' is equal to 1—using a process which comprises condensing a reactive ester of phenyl(oxo alkyl) of formula V, with 4-carboxamidopiperidine, reducing the (phenyl oxo alkyl)piperidine carboxamide by means of an alkali metal mixed hydride and recovering an alkyl piperidyl methylamine of formula III

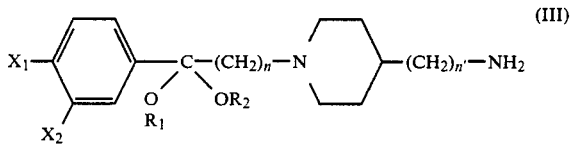
(III)

wherein the definitions of the substituents $X_1$, $X_2$, $R_1$, $R_2$ and n remain unaltered.

The reactive ester of phenyl oxo alkyl is preferably a chloride, a bromide, an iodide, a methane sulphonate or a p-toluene sulphonate.

The condensation with piperidine or with carboxamido piperidine is performed in a polar medium preferably in the presence of an alkli metal iodide. The polar solvent usually is pyridine, dimethylformamide, methyl ethylketone or hexamethyl phosphortriamide.

The alkali metal mixed hydride is a sodium or lithium aluminumhydride, sodium borohydride, potassium borohydride, lithium trimethoxy borohydride or lithium cyano borohydride.

The hydrolysis of the blocked piperidine is performed by functional exchange with an α-keto acid such as pyruvic acid, tartronic acid, mesoxalic acid or α-ketoglutaric acid. The following examples merely illustrate the invention. They do not limit it in any manner.

EXAMPLE I

1-[(4p.fluorophenyl 4-ethylenedioxy)butyl-1]4-[(N-cyano S-methyl)isothioureido methyl]piperidine

STEP A

1-[(4-p.fluorophenyl 4-ethylenedioxy)butyl-1]piperidine 4-carboxamide

A mixture of 66 g piperidine 4-carboxamide, 130 g 4-p.fluorophenyl 4,4-ethylenedioxy 1-chlorobutane, 75 g potassium carbonate and 1000 ml ethanol is heated to reflux for 18 hours under stirring. After separation, the filtrate is concentrated to dryness and the resulting paste is taken up with acetonitrile.

The resulting crystals are extensively washed with water then dried under vaccuum. 82 g of the pure title compound are obtained as colourless crystals, pure enough to be used for the further steps of the synthesis without any other purification. It melts at 145° C.

STEP B

1-[(4-p.-fluorophenyl 4-ethylenedioxy)butyl-1]4-aminomethyl piperidine 25 g of lithium aluminohydride are suspended in 300 ml tetrahydrofuran and to this suspension a solution of 80 g of 1-[(4-p.fluorophenyl 4-ethylenedioxy)butyl-1]piperidine 4-carboxamide in 600 ml tetrahydrofuran is added at room temperature. The whole mixture is then heated to reflux for one hour.

After cooling to room temperature, the excess reagent is hydrolysed by cautious addition of water and the precipitated alumina is filtered on celite. The clear filtrate is concentrated to dryness. The residue is taken up in ether, dried on sodium sulphate and evaporated off.

66 g of the desired amine are thus obtained as a viscous oil which is used as such for the next step of the synthesis.

STEP C

1-[(4-p.fluorophenyl 4-ethylenedioxy)butyl-1]4-[(N-cyano S-methylisothioureido)methyl]piperidine 66 g of 1-[(4-p.fluorophenyl 4-ethylenedioxy)butyl-1]4-aminomethyl piperidine and 29 g dimethyl cyanoimino dithiocarbonate are dissolved in 500 ml ethanol and heated to reflux for 2,5 hours. The reaction medium is thereafter concentrated to dryness and the oily residue is taken up with isopropyl ether from which it crystallizes.

After the crystals have been filtered, washed with isopropyl ether and dried, 78 g of the desired compound are recovered as colourless crystals melting at 124° C.

EXAMPLE II

1-[(4-p.fluorophenyl 4-ethylenedioxy)butyl-1]4-[(N-cyano N'-methyl)guanidinyl methyl]piperidine A solution of 10 g 1-[(4-fluorophenyl 4-ethylenedioxy)butyl]4-[(N-cyano S-methyl isothioureido)methyl]piperidine in 100 ml methanol is prepared into which a stream of methylamine is bubbled while keeping the reaction temperature to about 25°.

After absorption of 25 g methylamine, the mixture is stirred at room temperature.

The progress of the reaction is checked by TLC using as the eluting solvent a mixture of chloroform-isopropylamine (1:1).

After 3 hours, the reaction is complete and the mixture is concentrated to dryness to yield a viscous paste which crystallizes on taking up in ether. The crystalline mixture is set aside for a night then the crystals are separated by filtration, rinsed with ether and dried under vacuum. 8.5 g of colourless crystals are thus obtained which may be recrystallized for analysis from ethyl acetate. They melt at 152° C.

EXAMPLE III

1-[(4-p.fluorophenyl 4-oxo)butyl-1]4[(N-cyano N'-methyl)guanidinyl methyl]piperidine and its hydrochlorides A solution containing 3.5 g of 1-[(4-p.fluorophenyl 4-ethylenedioxy)butyl-1]4-[(N-cyano N'-methyl)guanidinyl methyl]piperidine and 60 ml N-hydrochloric acid is utilized and set aside at room temperature. After about 30 mn the mixture begins to crystallize. The crystals are separated by filtration, washed with the minimal amount of water then with cyclohexane.

After a further recrystallisation from acetonitrile 2.6 g of colourless crystals are obtained.

1-[(4-p.fluorophenyl 4-oxo)butyl-1]4-[(N-cyano N'-methyl)guanidinyl methyl]piperidine hydrochloride crystallizes with a mole of water. It melts at 214° C.

It may be easily converted into the free base by dissolving it in water, alkalinization of the aqueous phase by adding thereto sodium carbonate and extraction with ether. The ethereous phase is separated, dried over magnesium sulphate, decoloured with charcoal, filtered and evaporated to dryness.

1-[(4-p.fluorophenyl 4oxo)butyl-1]4-[(N-cyano N'-methyl)guanidinyl methyl]piperidine appears as an oily product.

EXAMPLE IV

1-[(4-p.fluorophenyl 4-oxo)butyl-1]4-[(N-cyano N'-propyl)guanidinylmethyl]piperidine

STEP A

A mixture of 5 g 1-[(4-p.fluorophenyl 4-ethylenedioxy)butyl-1]4-[(N-cyano S-methyl isothioureido)methyl]piperidine, 20 ml piperidine and 40 ml n-propylamine is heated to reflux for 17 hours.

After concentration to dryness and treatment with isopropyl ether, 4.7 g of 1-[(4-p.fluorophenyl 4-ethylenedioxy)butyl-1]4-[(N-cyano N'-propyl)guanidinyl methyl]piperidine are recovered as colourless crystals melting at 85°.

STEP B

The crystals of step A are promptly heated to reflux for 1 minute with 50 ml N-hydrochloric acid and 50 ml ethanol. The mixture is thereafter quickly cooled. Ethanol is expelled, the mixture is cooled in a water-bath, the solution is made alkaline with sodium hydroxide and extracted with chloroform. An oily product is thus obtained which is taken up in isopropyl ether from which it crystallizes. 3.2 g of the desired product are obtained as colourless crystals melting at about 84°.

EXAMPLE V

1-[(4-p.fluorophenyl 4-oxo)butyl-1]4[(N-cyano N'-allyl)guanidinyl methyl]piperidine

STEP A

1-[(4-p.fluorophenyl 4-ethylenedioxy)butyl-1]4-[(N-cyano N'-allyl)guanidinyl methyl]piperidine A mixture of 5 g 1-[(4-p.fluorophenyl 4-ethylenedioxy)butyl-1]4-[(N-cyano S-methylisothioureido)methyl]piperidine, 10 g pyridine and 30 g allylamine are heated to reflux for 3 h 30 mn. After concentration an oil is recovered which crystallizes by scratching with isopropyl ether.

After filtration of the ethereous solution, the crystals are washed then dried. 4.7 g of the ethylene ketal are obtained as colourless crystals melting at 85°.

STEP B 5 g of 1-[(4-p.fluorophenyl 4-ethylenedioxy)butyl-1]4-[(N-cyano N'-allyl)guanidinyl methyl]piperidine are dissolved in the cold in 250 ml of a N-solution of hydrochloric acid. The solution is kept for 17 hours at room temperature. One thereafter treats the reaction mixture with sodium hydroxide until basic and the aqueous solution is extracted with chloroform. The chloroformic solutions are washed with water and concentrated. An oily product is obtained which crystallizes from isopropyl ether, giving 2.5 g of colourless crystals melting at 90° C.

EXAMPLE VI

1[(4-p.fluorophenyl 4-oxo)butyl-1]4-[(N-cyano N'-cyclopropyl)guanidinyl methyl]piperidine

STEP A

1-[(4-p.fluorophenyl 4-ethylenedioxy)butyl-1]4-[(N-cyano N'-cyclopropyl)guanidinyl methyl]piperidine A mixture of 6 g 1-[(4-p.fluorophenyl 4-ethylenedioxy)butyl-1]4-[(N-cyano S-methylisothioureido)methyl]piperidine, 10 ml pyridine and 20 ml cyclopropylamine is prepared, concentrated to dryness and taken up with isopropyl ether which gives rise to crystals which are filtered, washed with isopropyl ether and dried. Melting point = 120° C.

STEP B

The selective hydrolysis of the ketal is performed by dissolving it in 150 ml N-solution of hydrochloric acid and 50 ml water. The mixture is kept for 17 hours at room temperature. After having made the medium basic and extracted it with ethyl acetate, 3.5 g of the desired 1-[(4-p.fluorophenyl 4-oxo)butyl-1]4-[(N-cyano N'-cyclopropyl)guanidinyl methyl]piperidine are obtained which may be recrystallized from acetonitrile. It melts at 153°–154° C.

EXAMPLE VII

1-[(4-p.fluorophenyl 4-oxo)butyl-1]4-[(N-cyano N'-morpholino guanidinyl)methyl]piperidine

STEP A

1-[(4-p.fluorophenyl 4-ethylenedioxy)butyl-1]4-[(N-cyano N'-morpholino guanidinyl)methyl]piperidine A mixture is made with 6 g 1-[(4-p.fluorophenyl 4-ethylenedioxy)butyl-1]4-[(N-cyano S-methylisothioureido)methyl]piperidine, 5 ml dimethylformamide and 30 ml morpholine and is heated to 100° for 4 hours. After this, the reaction mixture is allowed to cool to normal temperature. The excess reagent and solvent are distilled off under reduced pressure. The oily residue is taken up in 25 ml isopropyl ether and crystallisation is initiated by scratching. After a night in a cool place the crystals are separated by filtration, washed with isopropyl ether and dried.

3.75 g of the (N-cyano N'morpholino guanidine) are thus obtained which melt at 107°.

STEP B

1-[(4-p.fluorophenyl 4-oxo)butyl-1]4-[(N-cyano N'-morpholino guanidinyl)methyl]piperidine 3 g of 1-[(4-p.fluorophenyl 4-ethylenedioxy)butyl-1]4-[(N-cyano N'-morpholino guanidinyl)methyl]piperidine are dissolved in 100 ml water and 0.95 g oxalic acid. The mixture is kept for 12 hours at room temperature. 1-[(4-p.fluorophenyl 4-oxo)butyl-1]4-[(N-cyano N'morpholino guanidinyl)methyl]piperidine precipitates as the oxalic acid addition salt. It is separated by filtration, washed with cool water and dried under vacuum. It melts at about 225°–227° C.

The oxalate is converted to the free base by redissolving it in dioxan, alkalizing the solution by adding sodium carbonate and extracting it with methylene chloride. The chloromethylenic solution is separated, washed with water, dried over sodium sulphate and evaporated to dryness.

The oily residue is taken up in hot ethanol on cooling it crystallizes. 1-[(4-p.fluorophenyl 4-oxo)butyl-1]4-[(N-cyano N'-morpholinoguanidinyl)methyl]piperidine appears as colourless crystals melting at 121°–122°.

EXAMPLE VIII

1-[(4-p.fluorophenyl 4-oxo)butyl-1]4-[(N-cyano N-cyclohexyl guanidinyl)methyl]piperidine and its hydrochloride

STEP A

A mixture of 5 g 1-[(4-p.fluorophenyl 4-ethylenedioxy)butyl-1]4-[(N-cyano S-methyl isothioureido)methyl]piperidine, 10 g pyridine and 35 ml cyclohexylamine is heated to reflux for 6 hours. After having distilled off the excess of amine, an oily product is obtained which crystallizes by taking it up in few ml of isopropyl ether.

The mixture is set aside for some hours then the crystals are separated by filtration. They are dried, rinsed with a small amount of water then of isopropyl ether and finally they are dried under vacuum. 2.85 g of 1-[(4-fluoro phenyl 4-ethylenedioxy)butyl-1]4-[(N-cyano N'-cyclohexyl guanidinyl)methyl]piperidine are thus recovered which are crystallized from hot methanol on cooling. The pure compound melts at 131°–132° C.

STEP B

1-[(4-p.fluorophenyl 4-oxo)butyl-1]4-[(N-cyano N'-cyclohexyl guanidinyl)methyl]piperidine 2.4 g 1-[(4-p.fluorophenyl 4-ethylenedioxy)butyl-1]4-[(N-cyano N'-cyclohexyl guanidinyl)methyl]piperidine are dissolved in 100 ml water and 15 ml acetic acid. The whole mixture is kept at room temperature for 12 hours, it is then neutralized and extracted with methylene chloride. The methylenic phases are separated, washed with water then dried on sodium sulphate and evaporated to dryness.

The dry residue is taken up in hot ethyl acetate and on cooling it crystallizes. After drying 1.65 g of 1-[(4-p.fluorophenyl 4-oxo)butyl-1]4-[(N-cyano N'-cyclohexyl guanidinyl)methyl]piperidine are recovered as colourless crystals melting at 145°–146°.

EXAMPLE IX

In a similar manner the following compounds have been prepared:
(a) 1-(4-phenyl 4-oxo butyl-1)4-(N-cyano N'-allyl guanidinyl)piperidine which is solvated with one mol of water. MP=110°
The IR spectrum is in accordance with the structure.
(b) 1-(4-p.fluorophenyl 4-oxobutyl-1)4-(N-cyano N'-allyl guanidinyl)piperidine which melts at 160°. The IR spectrum is in accordance with the structure.
(c) 1-(4-p.fluorophenyl 4-oxobutyl-1)4-(N-cyano N'-methyl guanidinyl)piperidine which melts at 215° C. The IR spectrum is in accordance with the structure.

EXAMPLE X

Tablets containing 5 mg of 1-(4-p.fluorophenyl 4-oxo)butyl-1 4-(N-cyano N'-methyl guanidinyl)methyl piperidine

| Active ingedient | 5 g |
|---|---|
| Corn starch | 47 g 50 |
| Lactose | 40 g |
| Calcium phosphate | 35 g |
| Ethyl cellulose | 5 g |
| Talc | 10 g |
| Magnesium stearate | 7 g 50 |
| for 1000 tablets weighing in average | .150 g |

EXAMPLE XI

Pharmacological studies on the compounds according to the invention (a) Determination of the acute toxicity An approximate average lethal dose (LD50) has been determined after oral administration of the compounds according to the invention, at increasing doses, to batches of 10 female mice EOPS STRAIN (CESAL Breeding) using the method of D. E. J. Campbell and W. Richter (Acta Pharmacol and Toxicol 25 (1967) 345).

The animals were kept under survey for 5 days. The dead, if any, were counted. The average lethal doses range from 600 to 1780 mg/kg depending on the tested compounds.

Search of a possible action on the Central Nervous System

At high dosages (i.e. 60 mg/kg) the mice show a significant hypothermia, ptosis of the lids, a decrease of the motility and a decrease of the arousal response.

Determination of an anti-hypertensive action

This testing was carried out in batches of awakened male rats made hypertensive by ligation of the abdominal aorta.

The compounds according to this invention were given orally at doses of 2 mg, 5 mg and 10 mg/kg. They cause a clear and protracted decrease of the blood pressure.

Moreover the said compounds cause a strong hypotension at a dose of 100 and 500 µg/kg when administered to normotensive rats or normotensive dogs previously anaesthetized, intravenously.

Evidence of a vasodilating action

The compounds according to the invention induce a peripheral vasodilating effect which can be evidenced in the rats namely in the hind limbs which show, at the same time, an increase of 3° to 4° C. of the cutaneous temperature.

This effect appears, depending on the product, for doses ranging from 10 to 20 mg/kg.

This vasodilating effect is connected to a very marked inhibitory action on the diuresis.

What we claim is:
1. The phenyloxoalkyl piperidines of the formula

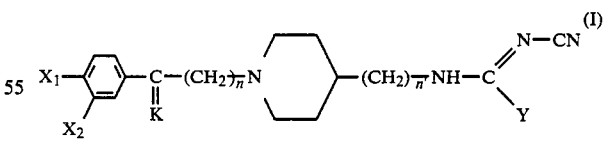

wherein
$X_1$ is hydrogen or fluoro, and
$X_2$ is hydrogen,
K is the oxygen of a ketonic group or the grouping

wherein $R_1$ and $R_2$ are a lower alkyl radical or together are a lower alkylene radical Y is selected from the group consisting of a radical $ZR_5$ wherein Z is an oxygen or a sulphur atom and $R_5$ is a lower alkyl radical or an amino group of the formula $$-N-R_3$$
$$\phantom{-N-}|$$
$$\phantom{-N-}R_4$$

wherein $R_3$ is a lower alkyl radical, a lower alkenyl radical, a lower cycloalkyl radical or morpholino $R_4$ is hydrogen n is 1, 2 or 3 n' is zero or 1 and the addition salts thereof with therapeutically acceptable acids.

2. The (N-cyano N'-alkyl guanidinyl)piperidines of the formula $I_A$ according to claim 1

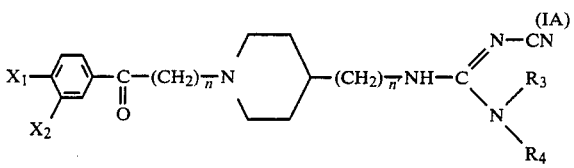

wherein the subtituents $X_1$, $X_2$, $R_3$, $R_4$, n and n' are as in claim 1.

3. The cyanoguanidines of the formula $I_D$

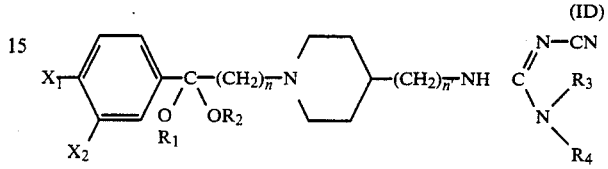

wherein $X_1$, $X_2$, $R_1$, $R_2$, $R_3$, $R_4$, n and n' are defined in claim 1.

4. A pharmaceutical composition containing as active ingredient at least one compound according to claim 1 in admixture or conjunction with a pharmaceutically acceptable carrier or vehicle.

5. A pharmaceutical composition according to claim 4 wherein the carrier or vehicle is one of those suitable for the parenteral, oral, rectal, percutaneous or sublingual way of administration.

6. A pharmaceutical composition according to claim 5 wherein the content of active ingredient ranges from 0.1 mg to 20 mg per unit dosage.

* * * * *